(12) United States Patent
Shi et al.

(10) Patent No.: US 11,151,732 B2
(45) Date of Patent: Oct. 19, 2021

(54) MOTION CORRECTION OF ANGIOGRAPHY IMAGES FOR 3D RECONSTRUCTION OF CORONARY ARTERIES

(71) Applicant: Siemens Healthcare GmbH, Erlangen (DE)

(72) Inventors: Bibo Shi, Monmouth Junction, NJ (US); Luis Carlos Garcia-Peraza Herrera, London (GB); Ankur Kapoor, Plainsboro, NJ (US); Mehmet Akif Gulsun, Lawrenceville, NJ (US); Tiziano Passerini, Plainsboro, NJ (US); Tommaso Mansi, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 30 days.

(21) Appl. No.: 16/744,295

(22) Filed: Jan. 16, 2020

(65) Prior Publication Data

US 2021/0225015 A1   Jul. 22, 2021

(51) Int. Cl.
*G06K 9/00*     (2006.01)
*G06T 7/37*     (2017.01)
*G06T 7/33*     (2017.01)
*A61B 6/00*     (2006.01)

(52) U.S. Cl.
CPC ............... *G06T 7/37* (2017.01); *A61B 6/504* (2013.01); *G06T 7/33* (2017.01); *G06T 2207/10116* (2013.01); *G06T 2207/30048* (2013.01); *G06T 2207/30101* (2013.01)

(58) Field of Classification Search
CPC ..................................................... G06T 7/37
See application file for complete search history.

(56) References Cited

U.S. PATENT DOCUMENTS

| 10,206,646 | B2 | 2/2019 | Gulsun et al. |
| 2010/0191541 | A1* | 7/2010 | Prokoski ................ A61B 5/418 705/2 |
| 2013/0094745 | A1* | 4/2013 | Sundar .................. G06T 3/0068 382/132 |

(Continued)

OTHER PUBLICATIONS

Xu et al., "Deaths: Final Data for 2016", National Vital Statistics Reports, 2018, vol. 67, No. 5, 1-76 pgs.

(Continued)

*Primary Examiner* — Oneal R Mistry (57) ABSTRACT

Systems and methods for computing a transformation for correction motion between a first medical image and a second medical image are provided. One or more landmarks are detected in the first medical image and the second medical image. A first tree of the anatomical structure is generated from the first medical image based on the one or more landmarks detected in the first medical image and a second tree of the anatomical structure is generated from the second medical image based on the one or more landmarks detected in the second medical image. The one or more landmarks detected in the first medical image are mapped to the one or more landmarks detected in the second medical image based on the first tree and the second tree. A transformation to align the first medical image and the second medical image is computed based on the mapping.

17 Claims, 7 Drawing Sheets

(56) References Cited

U.S. PATENT DOCUMENTS

2015/0089365 A1* 3/2015 Zhao .................. G06T 11/60
  715/708
2015/0342551 A1* 12/2015 Lavi .................. A61B 6/504
  600/431
2018/0350144 A1* 12/2018 Rathod ............. G06Q 20/3276

OTHER PUBLICATIONS

Benjamin et al., "Heart Disease and Stroke Statistics—2018 Update: A Report from the American Heart Association", Circulation, 2018, vol. 137, pp. e67-e492.

Çimen et al., "Reconstruction of Coronary Arteries from X-ray Angiography: A Review", Medical Image Analysis, Aug. 2016, vol. 32, pp. 46-68.

* cited by examiner

Receive a first medical image and a second medical image of an anatomical structure
202

Detect one or more landmarks in the first medical image and the second medical image
204

Generate a first tree of the anatomical structure from the first medical image based on the one or more landmarks detected in the first medical image and a second tree of the anatomical structure from the second medical image based on the one or more landmarks detected in the second medical image
206

Mapping the one or more landmarks detected in the first medical image to the one or more landmarks detected in the second medical image based on the first tree and the second tree
208

Compute a transformation to align the first medical image and the second medical image based on the mapping
210

Output the transformation
212

Compute a set of candidate mappings for a respective landmark in the first tree
402

↓

Filter the set of candidate mappings for the respective landmark to remove candidate mappings that are ancestry-violating
404

↓

Select a candidate mapping for the respective landmark from the filtered set of candidate mappings for the respective landmark
406

MOTION CORRECTION OF ANGIOGRAPHY IMAGES FOR 3D RECONSTRUCTION OF CORONARY ARTERIES

TECHNICAL FIELD

The present invention relates generally to motion correction of angiography images, and more particularly to motion correction of angiography images for 3D reconstruction of coronary arteries.

BACKGROUND

Coronary heart disease is caused by a blockage or narrowing (stenosis) of the arteries that supply blood to the heart, typically due to the accumulation of cholesterol plaque on the arterial walls. X-ray coronary angiography is an imaging modality for diagnosis and guidance of therapeutic procedures for coronary heart disease. X-ray coronary angiography is popular due to its ability to assist in both diagnosis and therapy of coronary heart disease, as well as its high spatio-temporal resolution. However, accurately reconstructing 3D coronary arteries from angiography images remains a challenge due to the loss of information from the projectional radiography. In particular, respiration motion must be accounted for in order to accurately reconstruct 3D coronary arteries.

BRIEF SUMMARY OF THE INVENTION

In accordance with one or more embodiments, systems and methods for computing a transformation to correct motion between a plurality of medical images are provided. One or more landmarks are detected in a first medical image and a second medical image. A first tree of the anatomical structure is generated from the first medical image based on the one or more landmarks detected in the first medical image and a second tree of the anatomical structure is generated from the second medical image based on the one or more landmarks detected in the second medical image. The one or more landmarks detected in the first medical image are mapped to the one or more landmarks detected in the second medical image based on the first tree and the second tree. A transformation to align the first medical image and the second medical image is computed based on the mapping.

In one embodiment, the first tree comprises the one or more landmarks detected in the first medical image, the second tree comprises the one or more landmarks detected in the second medical image, and the mapping is performed by, for each respective landmark of the one or more landmarks in the first tree, computing a set of candidate mappings between the respective landmark and the one or more landmarks in the second tree, filtering the set of candidate mappings to remove candidate mappings where a descendant of the respective landmark is not mapped to a descendant of a particular landmark of the candidate mapping in the second tree, and selecting a candidate mapping from the filtered set of candidate mappings based on a distance associated with each candidate mapping. The set of candidate mappings may comprise all possible mappings between the respective landmark and the one or more landmarks in the second tree.

In one embodiment, the transformation is computed by projecting the one or more landmarks detected in the first medical image to respective epipolar lines of the one or more landmarks in the second medical image, determining a transformation of the second medical image to move the one or more landmarks in the second medical image towards a closest point of its respective epipolar line, applying the transformation to the second medical image to move the one or more landmarks in the second medical image, and repeating the projecting, the determining, and the applying until a stopping condition is satisfied.

In one embodiment, the first tree is generated to include the one or more landmarks detected in the first medical image between a first start point and a first end point selected by a user and the second tree is generated to include the one or more landmarks detected in the second medical image between a second start point and a second end point selected by the user.

In one embodiment, the anatomical structure is a coronary artery and the one or more landmarks are detected by detecting one or more bifurcations of the coronary artery in the first medical image and the second medical image. The first medical image and the second medical image may be different views of the anatomical structure and may be x-ray angiography images.

In one embodiment, the one or more landmarks may be detected in one or more additional medical images of the anatomical structure, a tree of the anatomical structure may be generated for each respective image of the additional medical images based on the landmarks detected in the respective image, the landmarks detected in the first medical image may be mapped with the landmarks detected in the second medical image and the landmarks detected in the additional medical images, and the transformation may be computed to align the first medical image, the second medical image, and the additional medical images based on the mapping.

These and other advantages of the invention will be apparent to those of ordinary skill in the art by reference to the following detailed description and the accompanying drawings.

DETAILED DESCRIPTION

The present invention generally relates to methods and systems for motion correction of angiography images for 3D reconstruction of coronary arteries. Embodiments of the present invention are described herein to give a visual understanding of such methods and systems for motion correction of angiography images for 3D reconstruction of coronary arteries. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to motion correction of angiography images for 3D reconstruction of coronary arteries, the present invention is not so limited. Embodiments of the present invention may be applied for aligning images for any application.

Figure 1:
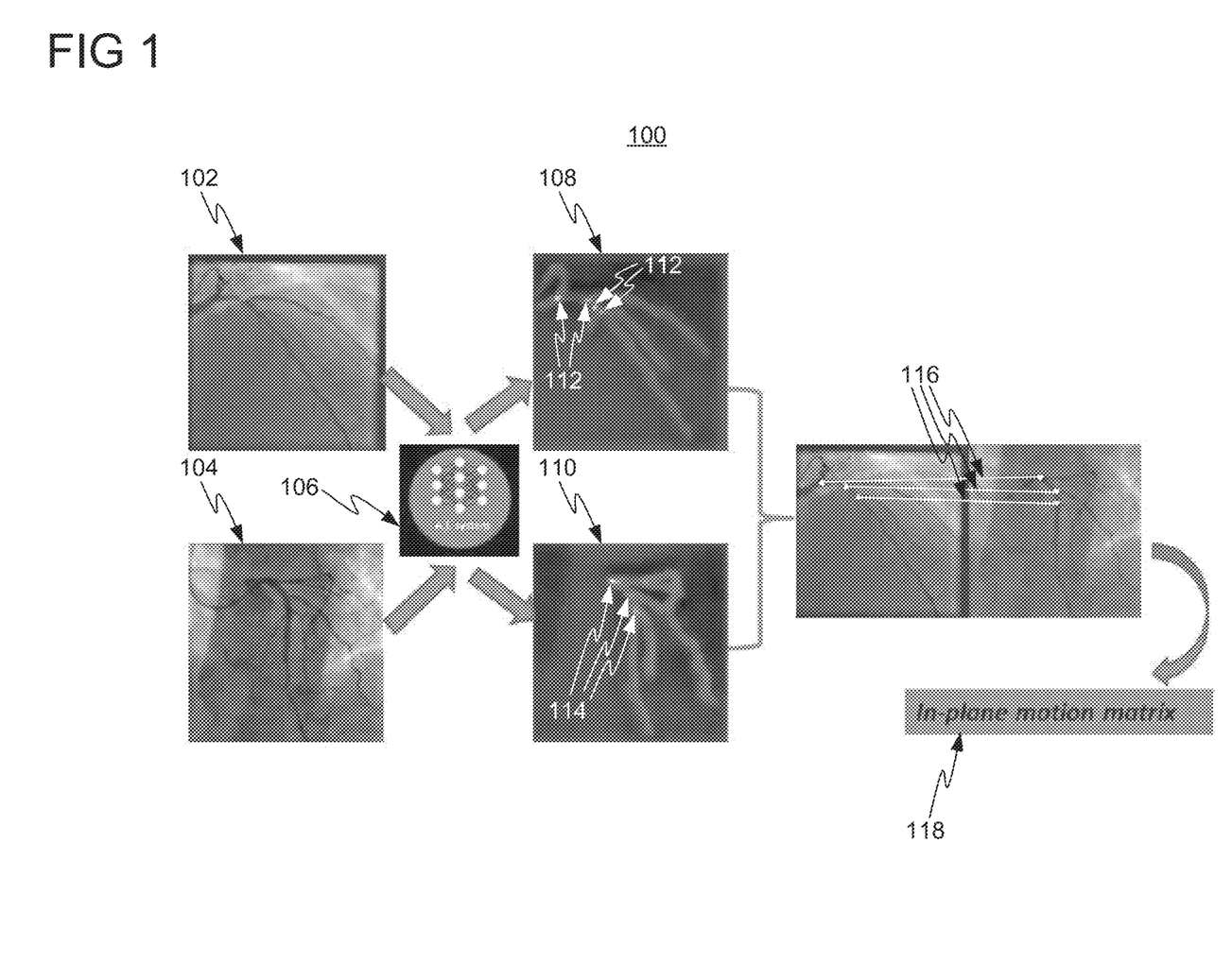
FIG. 1 shows a workflow for compensating motion between x-ray angiography images, in accordance with one or more embodiments.

FIG. 1 shows a workflow 100 for compensating motion between x-ray angiography images, in accordance with one or more embodiments. In workflow 100, x-ray angiography images 102 and 104 are input into an artificial intelligence (AI) system 106 trained for landmark detection. X-ray angiography images 102 and 104 are different views of a same coronary artery of a patient, and are not aligned due to respiratory motion of the patient during image acquisition. AI system 106 outputs heat map images 108 and 110 identifying bifurcations 112 and 114 (or other anatomical landmarks) of the coronary artery in x-ray angiography images 102 and 104, respectively. A mapping 116 between bifurcations 112 and 114 is determined and an in-plane motion matrix 118 is computed. In-plane motion matrix 118 represents a transformation to align x-ray angiography images 102 and 104 to spatially correspond with each other to thereby compensate for motion of the patient. In-plane motion matrix 118 may be used to transform bifurcations 114 of x-ray angiography image 104 to be closer to projected epipolar lines of bifurcations 112 of x-ray angiography image 102.

Figure 2:
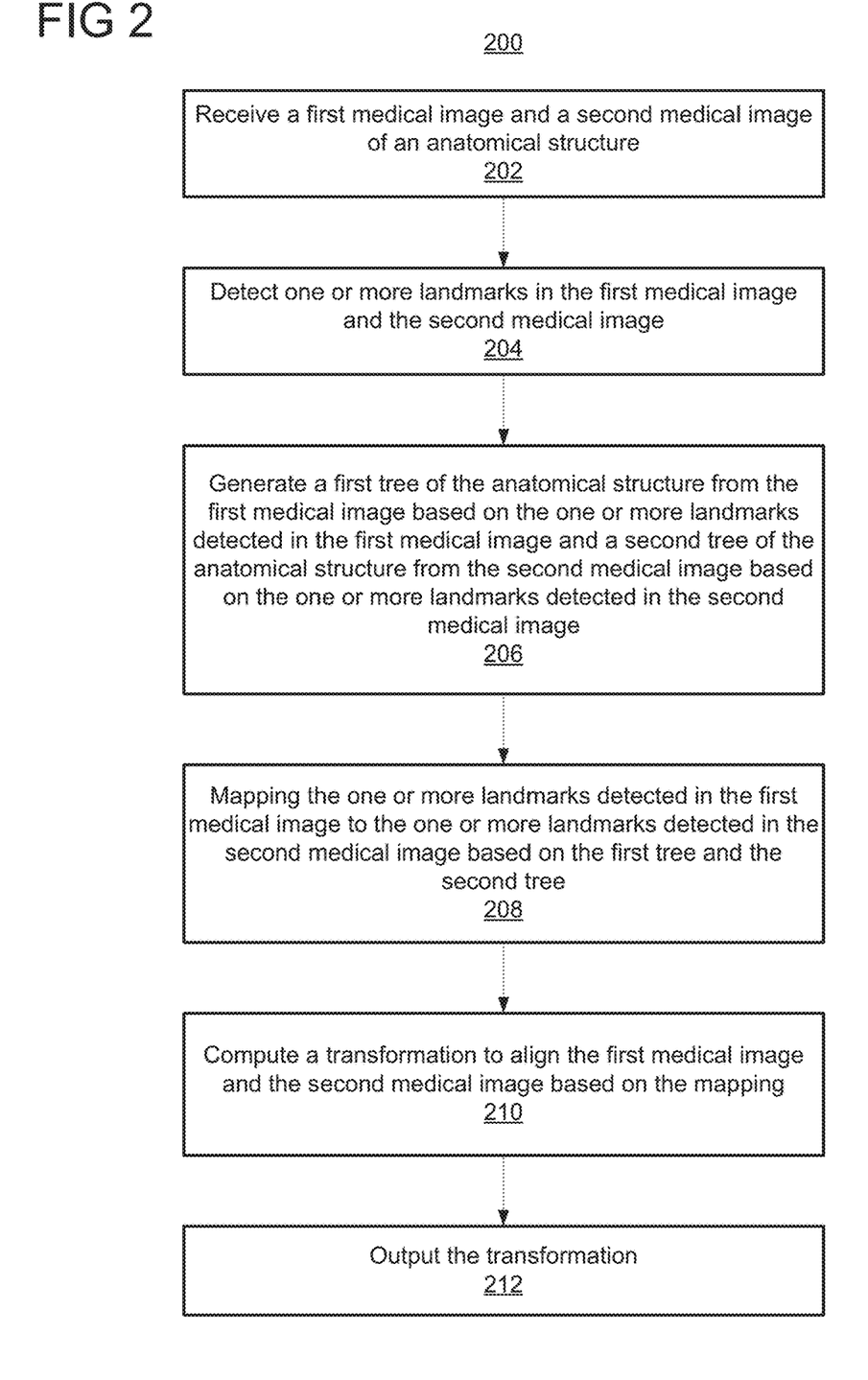
FIG. 2 shows a method for aligning medical images, in accordance with one or more embodiments.

FIG. 2 shows a method 200 for aligning medical images, in accordance with one or more embodiment. The steps of method 200 may be performed by any suitable computing device, such as, e.g., computer 702 of FIG. 7. Method 200 will be described with reference to workflow 100 of FIG. 1.

At step 202, a first medical image and a second medical image of an anatomical structure are received. In one embodiment, the anatomical structure is a coronary artery of a patient, however the anatomical structure may be any suitable anatomical structure of the patient. In one embodiment, the first medical image and the second medical image received at step 202 are x-ray angiography images 102 and 104 of FIG. 1 depicting a coronary artery.

In one embodiment, the first medical image and the second medical image depict different views of the anatomical structure. For example, the first medical image and the second medical image may be acquired at a same time or at different times at different positions with respect to the anatomical structure (e.g., with a certain separation angle between the acquisition of the first medical image and the second medical image). In another embodiment, the first medical image and the second medical image depict a same view of the anatomical structure acquired at different times, but at different states of deformation of the anatomical structure, e.g., due to motion (e.g., respiratory motion) of the patient.

In one embodiment, the first medical image and the second medical image are x-ray angiography images, however it should be understood that the first medical image and the second medical image may be of any suitable modality, such as, e.g., x-ray, magnetic resonance imaging (MRI), ultrasound (US), single-photon emission computed tomography (SPECT), positron emission tomography (PET), or any other suitable modality or combination of modalities. The first medical image and the second medical image may be received directly from an image acquisition device, such as, e.g., image acquisition device 714 of FIG. 7 (e.g., an x-ray scanner, etc.), used to acquire the medical images. Alternatively, the first medical image and the second medical image may be received by loading medical images previously stored on a memory or storage of a computer system (e.g., a picture archiving and communication system, PACS) or by receiving medical image data via network transmission from a remote computer system.

At step 204, one or more landmarks are detected in the first medical image and the second medical image. In one embodiment, for example where the anatomical structures is a coronary artery, the landmarks comprise corresponding bifurcations of the coronary artery detected in both the first medical image and the second medical image. Detecting such bifurcations is advantageous as the bifurcations define the geometry of the underlying coronary artery and generally coexist across different views of the coronary artery. The detected landmarks may be identified in any suitable form, such as, e.g., heat maps, binary maps, etc. In one embodiment, the landmarks detected at step 204 are bifurcations 112 and 114 identified on heat maps 108 and 110 detected from x-ray angiography images 102 and 104, respectively, in FIG. 1. In one embodiment, the landmarks comprise a catheter tip or stenosis. It should be understood that the landmarks may be any suitable landmark representing anatomically meaningful locations on organs, bones, blood vessels, etc.

Figure 3:
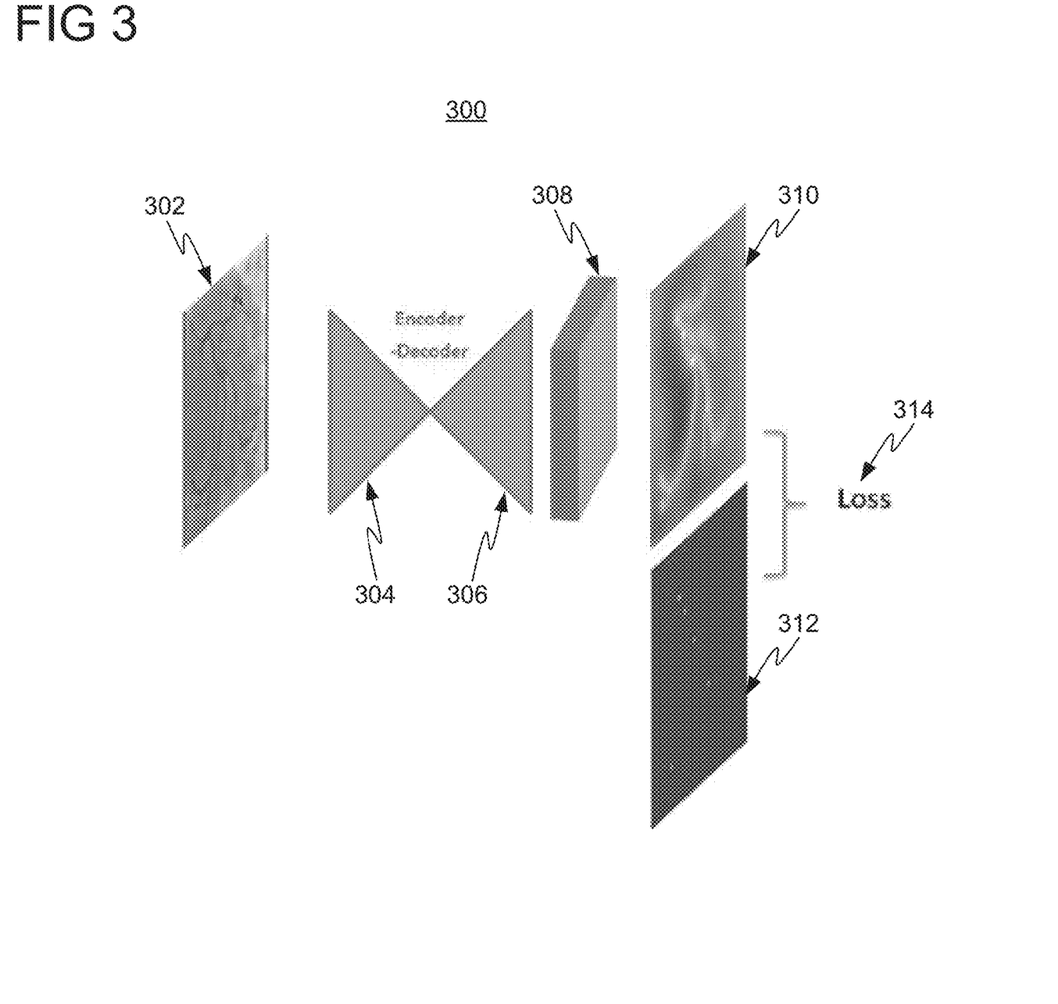
FIG. 3 shows a network architecture for training a fully convolutional network, in accordance with one or more embodiments.

In one embodiment, the landmarks are detected using a machine learning network. Such machine learning network is illustratively represented as AI system 106 in FIG. 1. In one example, the machine learning network may be a fully convolutional network (FCN) having an encoder-decoder structure, as shown in FIG. 3. However, it should be understood that the machine learning network may have any suitable design or architecture, and is not limited to the network architecture shown in FIG. 3.

FIG. 3 shows a network architecture 300 for training an FCN, in accordance with one or more embodiments. As shown in FIG. 3, the FCN has an encoder-decoder structure comprising encoder 304 and decoder 306. During a training or offline stage, as shown in FIG. 3, encoder 304 receives as input a training image 302 (e.g., an x-ray angiography training image) depicting a coronary artery and codes training image 302 into a code that is substantially less in size than that of training image 302. Decoder 306 decodes the code to generate heat map 310 identifying bifurcations of the coronary artery depicted in training image 302. Layer 308 is the last layer of feature tensors before the final output layer. All the intermediate information generated in encoder 304 is shared with decoder 306 so that no information is lost in the encoding process. A training loss 314 is defined between heat map 310 and ground truth annotated image 312 of bifurcations in training image 302. The locations of the bifurcations in ground truth annotated image 312 are diffused with Gaussian blurring to account for the uncertainty of annotators and to ease the training. During an online or inference stage, the trained FCN may be applied to detect landmarks in the first medical image and the second medical image at step 204 of FIG. 2, in accordance with one embodiment. In particular, the trained FCN receives one or more input images (e.g., the first medical image and the second medical image received at step 202 of FIG. 2) and outputs a heat map for each input image identifying landmarks in that input image. The heat map has the same resolution and size as the input image. The location (e.g., coordinates) of the landmarks may be determined by applying image process techniques, such as, e.g., thresholding and independent component analysis. In one embodiment, in addition to the one or more input images, temporally neighboring frames are also input into the trained FCN. In one embodiment, the input images include a channel comprising a centerline of the coronary artery in the input images, which may serve as an attention map and improve the overall detection performance.

At step 206 of FIG. 2, a first tree of the anatomical structure is generated from the first medical image based on the one or more landmarks detected in the first medical image and a second tree of the anatomical structure is generated from the second medical image based on the one or more landmarks detected in the second medical image. The trees comprise a plurality of points representing a path from a start point on the anatomical structure to one or more end points in the first medical image and the second medical image. For example, where the anatomical structure is a coronary artery, the trees comprise a plurality of points representing a path from a root of the coronary artery to one or more leaves of the coronary artery.

The start and end points are defined in the first medical image and the second medical image based on input received from a user (e.g., a clinician). For example, a user may interact with a computing device (e.g., using a mouse) to select seeds defining the start and end points of the anatomical structure in the first medical image and in the second medical image. The first tree is generated based on the first medical image, the landmarks detected in the first medical image, and the start and end points defined in the first medical image. The second tree is generated based on the second medical image, the landmarks detected in the second medical image, and the start and end points defined in the second medical image. The first tree and the second tree are generated to include points corresponding to the detected landmarks in the first medical image and the second medical image, respectively. The first tree and the second tree may be automatically constructed based on, e.g., tracking-based methods, graph-based methods, or any other suitable method. In one embodiment, the first tree and the second tree are generated according to the method disclosed in U.S. Pat. No. 10,206,646, entitled "Method and System for Extracting Centerline Representation of Vascular Structures in Medical Images via Optimal Paths in Computational Flow Fields," the disclosure of which is incorporated herein by reference in its entirety.

At step 208, the one or more landmarks detected in the first medical image are mapped to the one or more landmarks detected in the second medical image based on the first tree and the second tree. FIG. 1 illustratively shows mappings 116 between landmarks, in accordance with one embodiment. The mapping may be represented as a non-surjective injective mapping function M that maps each landmark in the first tree (i.e., each landmark detected in the first medical image) to a same corresponding landmark in the second tree (i.e., a same corresponding landmark detected in the second medical image). Formally, given the first tree T1(V1, E1) having vertices V1 representing points in tree T1 and edges E1 connecting the vertices V1 and the second tree T2(V2, E2) having vertices V2 representing points in tree T2 and edges E2 connecting the vertices V2, mapping function M matches a landmark n1 $\varepsilon$T1 to a landmark M(n1)$\varepsilon$T2. In one embodiment, an optimal mapping M* of landmarks in the first tree to corresponding landmarks in the second tree is determined according method 400 of FIG. 4. In one embodiment, the mapping may be determined for all points in the first tree and the second tree, and is not limited to the landmarks.

Figure 4:
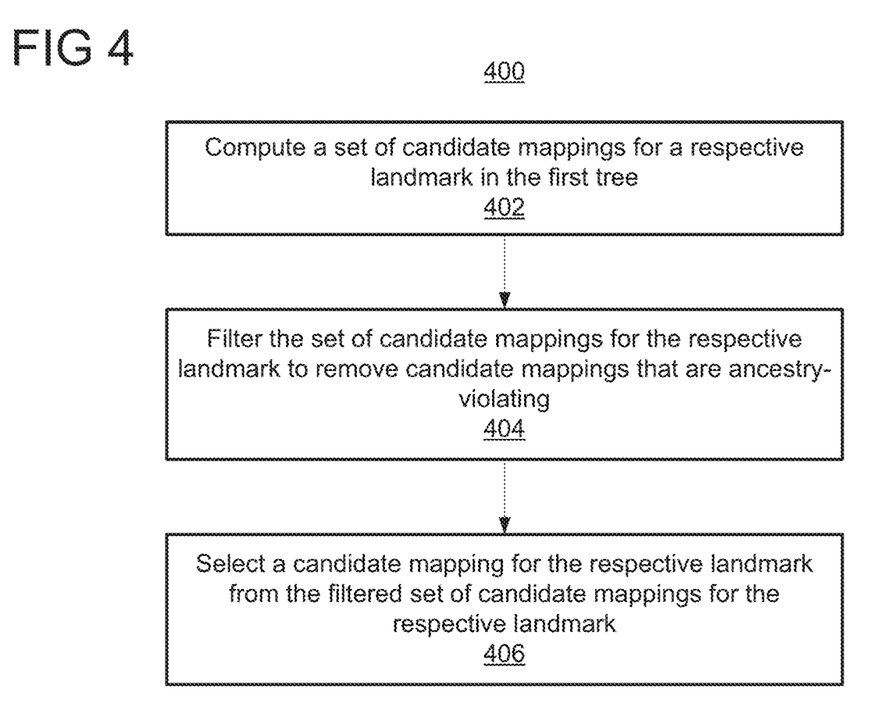
FIG. 4 shows a method for mapping a landmark in a first tree to a same corresponding landmark in a second tree, in accordance with one or more embodiments.

FIG. 4 shows a method 400 for mapping a landmark in a first tree to a same corresponding landmark in a second tree, in accordance with one or more embodiments. The steps of method 400 may be performed at step 208 of FIG. 2 for each respective landmark in the first tree.

At step 402, a set of candidate mappings for the respective landmark in the first tree is computed. The set of candidate mappings for the respective landmark in the first tree represents all possible mappings between the respective landmark in the first tree and landmarks in the second tree. If the first tree and the second tree have a different number of landmarks, a mapping of N points is performed, where N is the number of landmarks in the tree having the fewest landmark.

At step 404, the set of candidate mappings for the respective landmark in the first tree is filtered to remove candidate mappings that are ancestry-violating. A candidate mapping for a respective landmark n1 is ancestry-violating if a descendant of the respective landmark n1$\varepsilon$T1 is not mapped to a descendant of a landmark M(n1) $\varepsilon$T2 of the candidate mapping. A descendent of a landmark is any point further down the tree, from the start point to the end point. A candidate mapping that is not ancestry-violating is considered to be ancestry-respectful.

At step 406, a candidate mapping is selected for the respective landmark in the first tree from the filtered set of candidate mappings for the respective landmark of the first tree. In one embodiment, the candidate mapping that has a minimum cost is selected from the set of candidate mappings. For example, in one embodiment, the candidate mapping having a minimum cost may be the candidate mapping associated with a shortest distance (e.g., Euclidean distance metric) to epipolar lines. Specifically, in one embodiment, for each candidate mapping, a landmark P1 in image A is mapped to a landmark P2 in image B. As the landmark P1 in image A is projected to an epipolar line L1 in image B, the Euclidean distance may be calculated between L1 and P2 as the cost. The sum of all Euclidean distances between landmarks in image B and the projected epipolar lines from image A is the overall cost for this candidate mapping. Among all candidate mappings, the one that has the minimum cost will be the final optimal one. In another embodiment, the candidate mapping having a minimum cost may be determined based on the position of the candidate mapping relative to the epipolar line. Specifically, the epipolar line separates the images into two regions and different costs may be associated with the candidate mapping based on which region the candidate mapping is located. It should be understood that the cost may be any other suitable metric.

In one embodiment, method 400 is not performed for each landmark in the first tree. Instead the quality of the mapping is compared for a different number of landmarks, not necessarily all landmarks in the first tree. This will make the mapping more robust to bifurcation false positive detection. In another embodiment, method 400 is performed for all points in the first tree and is not limited to the landmarks in the first tree.

At step 210 of FIG. 2, a transformation to align the first medical image and the second medical image is computed based on the mapping. In one embodiment, the transformation is a motion compensation transformation for compensating for motion (e.g., respiratory motion) of the patient. In one embodiment, the transformation may be an in-plane motion matrix, as illustratively shown as in-plane motion matrix 118 in FIG. 1, however the transformation may be in any suitable form. The transformation may be computed according to method 500 of FIG. 5, in accordance with one embodiment.

Figure 5:
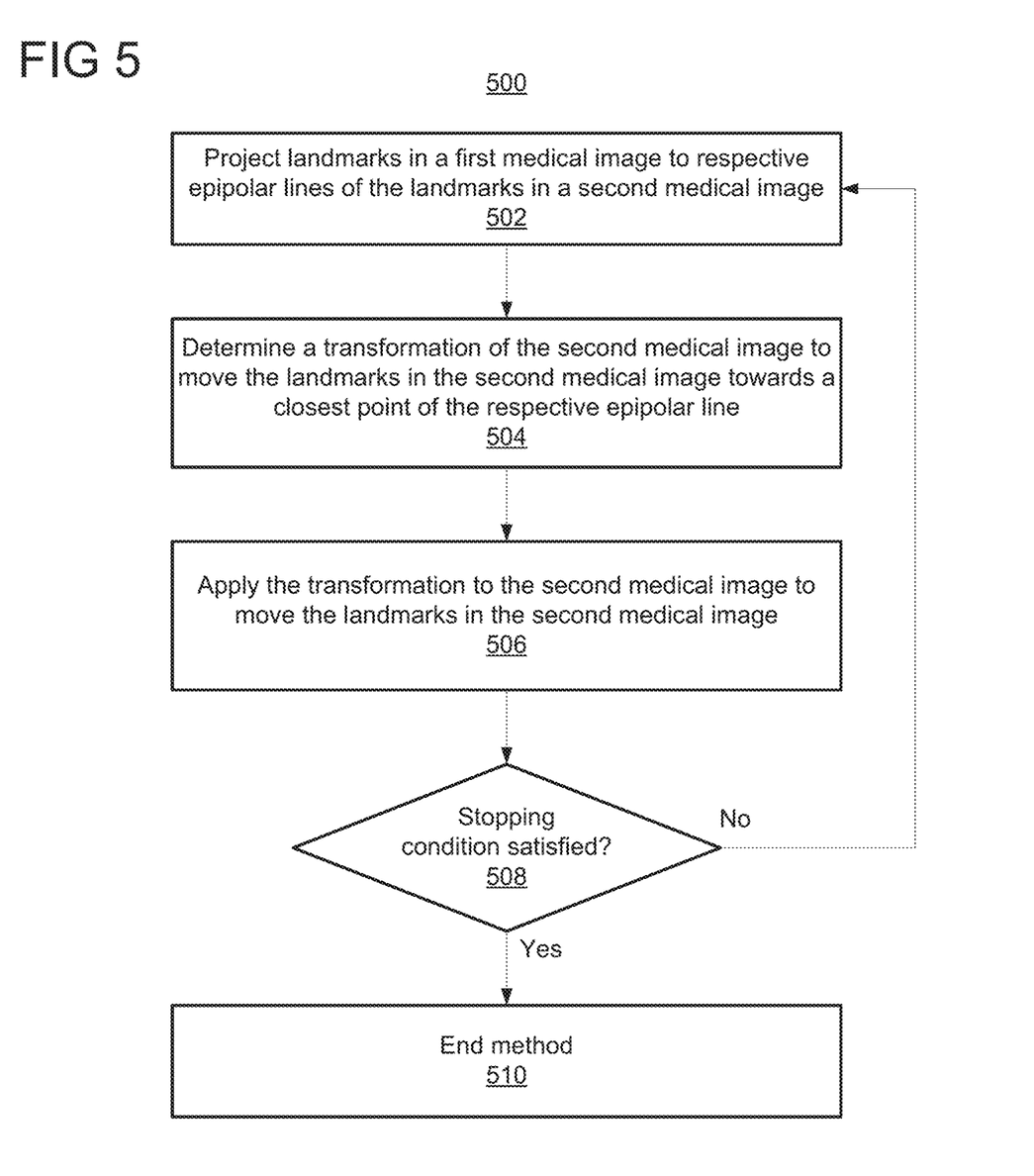
FIG. 5 shows a method for determining a transformation to align a first medical image and a second medical image, in accordance with one or more embodiments.

FIG. 5 shows a method 500 for determining a transformation to align a first medical image and a second medical image, in accordance with one or more embodiments. The steps of method 500 may be performed at step 210 of FIG. 2.

At step 502, landmarks in the first medical image are projected to respective epipolar lines of the landmarks in the second medical image. An epipolar line in the second medical image represent possible points in the second medical image where a particular landmark depicted in the first medical image may be located.

Figure 6:
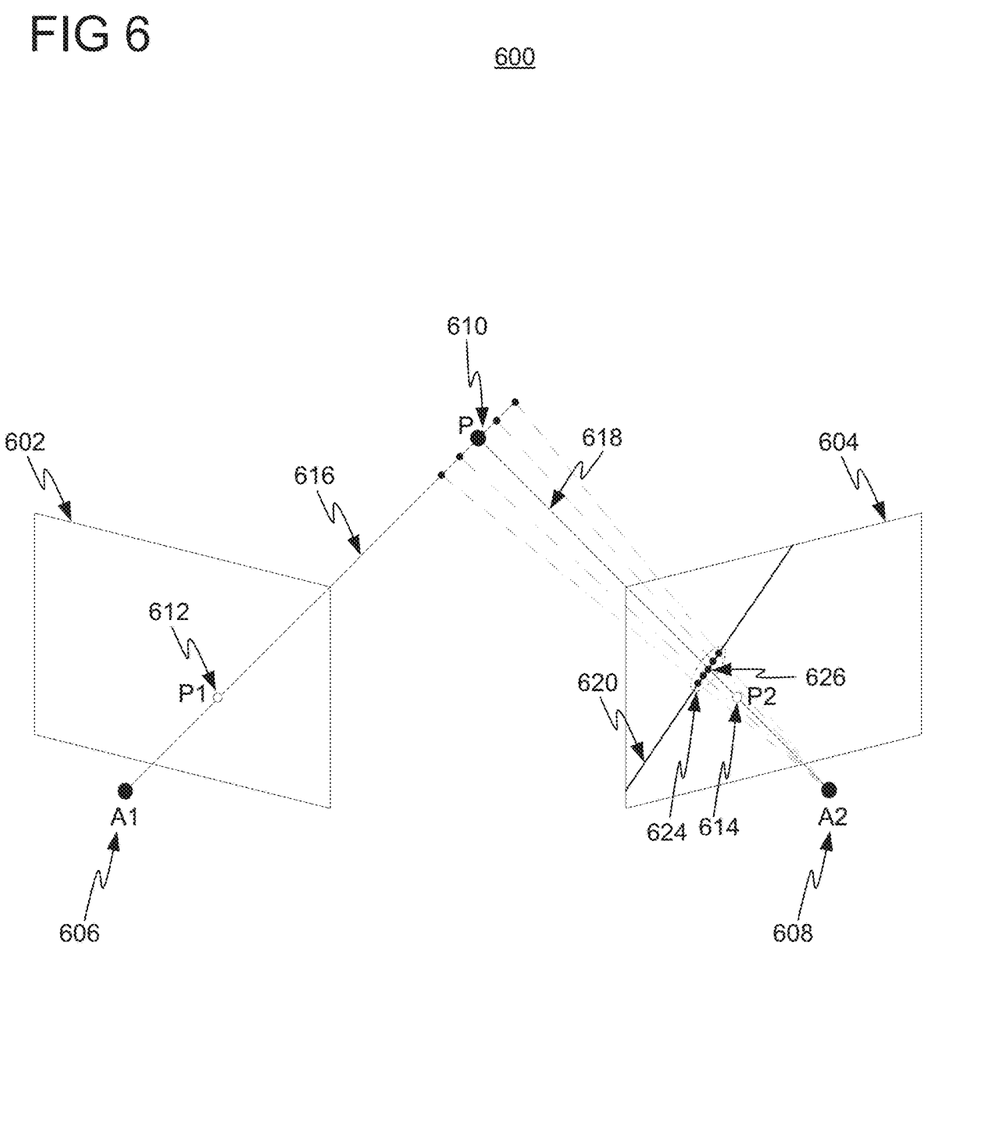
FIG. 6 shows a schematic diagram depicting epipolar geometry of a landmark depicted in different imaging planes, in accordance with one or more embodiments.

Referring to FIG. 6, a schematic diagram 600 is shown illustratively depicting epipolar geometry of a landmark visualized in different imaging planes, in accordance with one or more embodiments. Schematic diagram 600 shows imaging plane 602 of a landmark P 610 acquired by image acquisition device A1 606 and imaging plane 604 of landmark P 610 acquired by image acquisition device A2 608, which may be the same or different than image acquisition device A1 606. In one embodiment, imaging plane 602 is the first medical image, imaging plane 604 is the second medical image, and landmark P1 612 is the respective landmark in method 500 of FIG. 5. It should be understood that landmark P 610 may be located between image acquisition devices A1 606 and A2 608 and imaging planes 602 and 604, respectively, where, e.g., image acquisition devices A1 606 and A2 608 are x-ray image acquisition devices.

Landmark P 610 is captured in imaging plane 602 by image acquisition device A1 606 along line of sight 616 as point P1 612 and in imaging plane 604 by image acquisition device A2 608 along line of sight 618 as point P2 614. When projecting point P1 612 in imaging plane 602 to imaging plane 604, point P1 612 may be located along any point of line of sight 616 that is visible in imaging plane 604, such as exemplary candidate points 624. The portion of line of sight 616 visible in imaging plane 604 is referred to as an epipolar line 620.

At step 504 of FIG. 5, a transformation X of the second medical image is determined to move the landmarks in the second medical image towards a closest point of its respective epipolar line. The transformation X may be any transformation, such as, e.g., rigid or affine transformations, depending on the number of landmarks. The closest point may be determined based on the Euclidean distance or any other suitable distance metric. As shown in FIG. 6, a transformation X is determined that transforms imaging plane 604 to move point P2 614 towards point 626.

At step 506, the transformation X is applied to the second medical image to move the landmarks in the second medical image.

At step 508, it is determined whether a stopping condition is satisfied. In one embodiment, the stopping condition is satisfied when the transformation X converges (i.e., is close to an identity matrix). In another embodiment, the stopping condition is satisfied after a predetermined number of iterations. Other criteria for the stopping condition are also contemplated. If the stopping condition is not satisfied at step 508, method 500 returns to step 502 for another iteration. If the stopping condition is satisfied at step 508, method 500 ends at step 510. The transformation determined after one or more iterations of method 500 represents the transformation to align the first medical image and the second medical image.

At step 212 of FIG. 2, the transformation is output. For example, the transformation can be output by displaying the transformation on a display device of a computer system, storing the transformation on a memory or storage of a computer system, or by transmitting the transformation to a remote computer system.

Advantageously, embodiments of the present invention provide for an automatic landmark detection and motion correction method. In one embodiment, the embodiments of the present invention may be applied to correct motion between the first medical image and the second medical image for 3D reconstruction of a coronary artery.

It should be understood that while method 200 of FIG. 2 is described for aligning a first medical image and a second medical image, the present invention may be applied to align any plurality of medical images. For example, the one or more landmarks may be detected in one or more additional medical images of the anatomical structure, a tree of the anatomical structure may be generated for each respective image of the additional medical images based on the landmarks detected in the respective image, step 208 may be performed by mapping the landmarks detected in the first medical image with the landmarks detected in the second medical image and the landmarks detected in the additional medical images, and step 210 may be performed by computing the transformation to align the first medical image, the second medical image, and the additional medical images based on the mapping.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2 and 4-5. Certain steps or functions of the methods and workflows described herein, including one or more of the steps or functions of FIGS. 2 and 4-5, may be performed by a server or by another processor in a network-based cloud-computing system. Certain steps or functions of the methods and workflows described herein, including one or more of the steps of FIGS. 2 and 4-5, may be performed by a client computer in a network-based cloud computing system. The steps or functions of the methods and workflows described herein, including one or more of the steps of FIGS. 2 and 4-5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2 and 4-5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
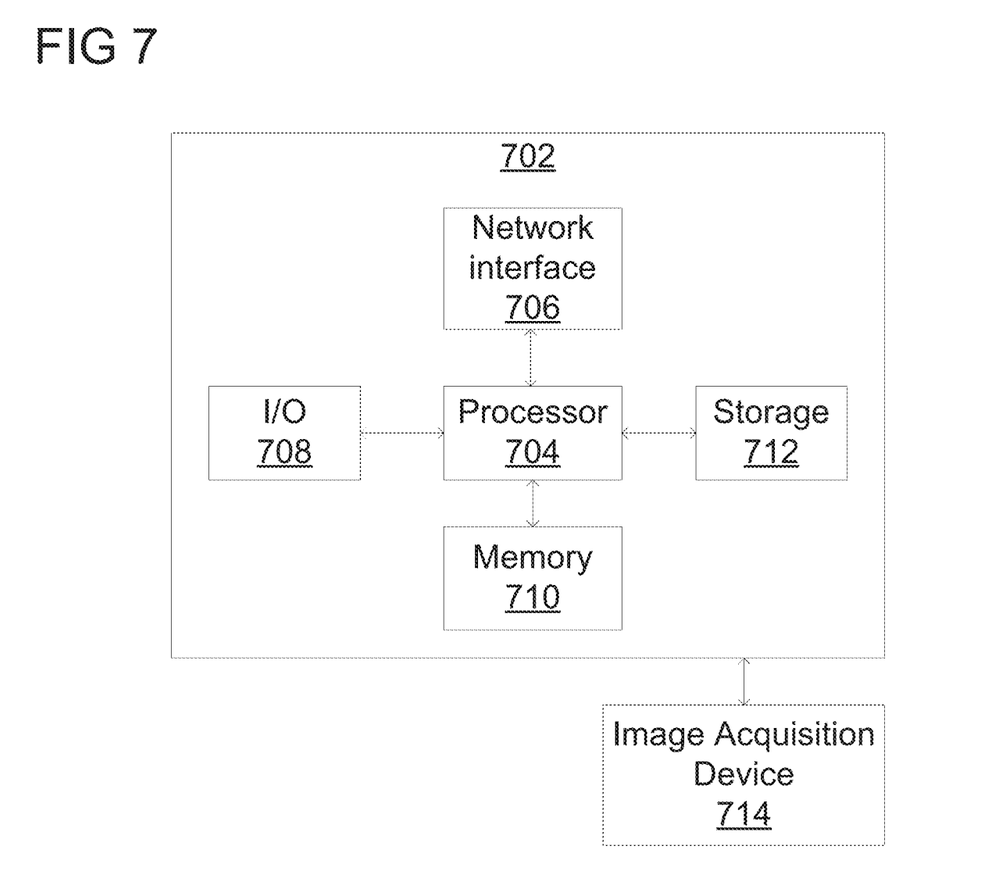
FIG. 7 shows a high-level block diagram of a computer.

A high-level block diagram of an example computer 702 that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method and workflow steps or functions of FIGS. 2 and 4-5 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIGS. 2 and 4-5. Accordingly, by executing the computer program instructions, the processor 704 executes the method and workflow steps or functions of FIGS. 2 and 4-5. Computer 702 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

An image acquisition device 714 can be connected to the computer 702 to input image data (e.g., medical images) to the computer 702. It is possible to implement the image acquisition device 714 and the computer 702 as one device. It is also possible that the image acquisition device 714 and the computer 702 communicate wirelessly through a network. In a possible embodiment, the computer 702 can be located remotely with respect to the image acquisition device 714.

Any or all of the systems and apparatus discussed herein may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:
1. A method comprising:
    detecting one or more landmarks in a first medical image of an anatomical structure and a second medical image of the anatomical structure;
    generating a first tree of the anatomical structure from the first medical image based on the one or more landmarks detected in the first medical image and a second tree of the anatomical structure from the second medical image based on the one or more landmarks detected in the second medical image;

mapping the one or more landmarks detected in the first medical image to the one or more landmarks detected in the second medical image based on the first tree and the second tree; and computing a transformation to align the first medical image and the second medical image based on the mapping;

wherein the first tree comprises the one or more landmarks detected in the first medical image, the second tree comprises the one or more landmarks detected in the second medical image, and mapping the one or more landmarks detected in the first medical image to the one or more landmarks detected in the second medical image based on the first tree and the second tree comprises:

for each respective landmark of the one or more landmarks in the first tree:

computing a set of candidate mappings between the respective landmark and the one or more landmarks in the second tree;

filtering the set of candidate mappings to remove candidate mappings where a descendant of the respective landmark is not mapped to a descendant of a particular landmark of the candidate mapping in the second tree; and selecting a candidate mapping from the filtered set of candidate mappings based on a distance associated with each candidate mapping.

2. The method of claim 1, wherein the set of candidate mappings comprises all possible mappings between the respective landmark and the one or more landmarks in the second tree.

3. The method of claim 1, wherein computing a transformation to align the first medical image and the second medical image based on the mapping comprises:

projecting the one or more landmarks detected in the first medical image to respective epipolar lines of the one or more landmarks in the second medical image;

determining a transformation of the second medical image to move the one or more landmarks in the second medical image towards a closest point of its respective epipolar line;

applying the transformation to the second medical image to move the one or more landmarks in the second medical image; and repeating the projecting, the determining, and the applying until a stopping condition is satisfied.

4. The method of claim 1, wherein generating a first tree of the anatomical structure from the first medical image based on the one or more landmarks detected in the first medical image and a second tree of the anatomical structure from the second medical image based on the one or more landmarks detected in the second medical image comprises:

generating the first tree to include the one or more landmarks detected in the first medical image between a first start point and a first end point selected by a user; and generating the second tree to include the one or more landmarks detected in the second medical image between a second start point and a second end point selected by the user.

5. The method of claim 1, wherein the anatomical structure is a coronary artery.

6. The method of claim 5, wherein detecting one or more landmarks in a first medical image of an anatomical structure and a second medical image of the anatomical structure comprises:

detecting one or more bifurcations of the coronary artery in the first medical image and the second medical image.

7. The method of claim 1, wherein the first medical image and the second medical image are different views of the anatomical structure.

8. The method of claim 1, wherein the first medical image and the second medical image are x-ray angiography images.

9. The method of claim 1, further comprising:

detecting the one or more landmarks in one or more additional medical images of the anatomical structure; and generating a tree of the anatomical structure for each respective image of the one or more additional medical images based the one or more landmarks detected in the respective image;

wherein mapping the one or more landmarks detected in the first medical image to the one or more landmarks detected in the second medical image based on the first tree and the second tree comprises:

mapping the one or more landmarks detected in the first medical image with the one or more landmarks detected in the second medical image and the one or more landmarks detected in the one or more additional medical images; and wherein computing a transformation to align the first medical image and the second medical image based on the mapping comprises:

computing the transformation to align the first medical image, the second medical image, and the one or more additional medical images based on the mapping.

10. An apparatus, comprising:

means for detecting one or more landmarks in a first medical image of an anatomical structure and a second medical image of the anatomical structure;

means for generating a first tree of the anatomical structure from the first medical image based on the one or more landmarks detected in the first medical image and a second tree of the anatomical structure from the second medical image based on the one or more landmarks detected in the second medical image;

means for mapping the one or more landmarks detected in the first medical image to the one or more landmarks detected in the second medical image based on the first tree and the second tree; and means for computing a transformation to align the first medical image and the second medical image based on the mapping;

wherein the first tree comprises the one or more landmarks detected in the first medical image, the second tree comprises the one or more landmarks detected in the second medical image, and the means for mapping the one or more landmarks detected in the first medical image to the one or more landmarks detected in the second medical image based on the first tree and the second tree comprises:

means for computing a set of candidate mappings for each respective landmark of the one or more landmarks in the first tree, each comprising candidate mappings between the respective landmark and the one or more landmarks in the second tree;

means for filtering the set of candidate mappings for each respective landmark in the first tree to remove candidate mappings where a descendant of the respective landmark is not mapped to a descendant of a particular landmark of the candidate mapping in the second tree; and means for selecting a candidate mapping from the filtered set of candidate mappings for each respective landmark in the first tree based on a distance associated with each candidate mapping.

11. The apparatus of claim 10, wherein the set of candidate mappings comprises all possible mappings between the respective landmark and the one or more landmarks in the second tree.

12. The apparatus of claim 10, wherein the means for computing a transformation to align the first medical image and the second medical image based on the mapping comprises:

means for projecting the one or more landmarks detected in the first medical image to respective epipolar lines of the one or more landmarks in the second medical image;

means for determining a transformation of the second medical image to move the one or more landmarks in the second medical image towards a closest point of its respective epipolar line;

means for applying the transformation to the second medical image to move the one or more landmarks in the second medical image; and means for repeating the projecting, the determining, and the applying until a stopping condition is satisfied.

13. The apparatus of claim 10, wherein the means for generating a first tree of the anatomical structure from the first medical image based on the one or more landmarks detected in the first medical image and a second tree of the anatomical structure from the second medical image based on the one or more landmarks detected in the second medical image comprises:

means for generating the first tree to include the one or more landmarks detected in the first medical image between a first start point and a first end point selected by a user; and means for generating the second tree to include the one or more landmarks detected in the second medical image between a second start point and a second end point selected by the user.

14. A non-transitory computer readable medium storing computer program instructions, the computer program instructions when executed by a processor cause the processor to perform operations comprising:

detecting one or more landmarks in a first medical image of an anatomical structure and a second medical image of the anatomical structure;

generating a first tree of the anatomical structure from the first medical image based on the one or more landmarks detected in the first medical image and a second tree of the anatomical structure from the second medical image based on the one or more landmarks detected in the second medical image;

mapping the one or more landmarks detected in the first medical image to the one or more landmarks detected in the second medical image based on the first tree and the second tree; and computing a transformation to align the first medical image and the second medical image based on the mapping;

wherein the first tree comprises the one or more landmarks detected in the first medical image, the second tree comprises the one or more landmarks detected in the second medical image, and mapping the one or more landmarks detected in the first medical image to the one or more landmarks detected in the second medical image based on the first tree and the second tree comprises:

for each respective landmark of the one or more landmarks in the first tree:

computing a set of candidate mappings between the respective landmark and the one or more landmarks in the second tree;

filtering the set of candidate mappings to remove candidate mappings where a descendant of the respective landmark is not mapped to a descendant of a particular landmark of the candidate mapping in the second tree; and selecting a candidate mapping from the filtered set of candidate mappings based on a distance associated with each candidate mapping.

15. The non-transitory computer readable medium of claim 14, wherein computing a transformation to align the first medical image and the second medical image based on the mapping comprises:

projecting the one or more landmarks detected in the first medical image to respective epipolar lines of the one or more landmarks in the second medical image;

determining a transformation of the second medical image to move the one or more landmarks in the second medical image towards a closest point of its respective epipolar line;

applying the transformation to the second medical image to move the one or more landmarks in the second medical image; and repeating the projecting, the determining, and the applying until a stopping condition is satisfied.

16. The non-transitory computer readable medium of claim 15, wherein detecting one or more landmarks in a first medical image of an anatomical structure and a second medical image of the anatomical structure comprises:

detecting one or more bifurcations of a coronary artery in the first medical image and the second medical image.

17. The non-transitory computer readable medium of claim 14, the operations further comprising:

detecting the one or more landmarks in one or more additional medical images of the anatomical structure; and generating a tree of the anatomical structure for each respective image of the one or more additional medical images based the one or more landmarks detected in the respective image;

wherein mapping the one or more landmarks detected in the first medical image to the one or more landmarks detected in the second medical image based on the first tree and the second tree comprises:

mapping the one or more landmarks detected in the first medical image with the one or more landmarks detected in the second medical image and the one or more landmarks detected in the one or more additional medical images; and wherein computing a transformation to align the first medical image and the second medical image based on the mapping comprises:

computing the transformation to align the first medical image, the second medical image, and the one or more additional medical images based on the mapping.

* * * * *